United States Patent
Gonzalez et al.

(12) 
(10) Patent No.: US 6,531,118 B1
(45) Date of Patent: Mar. 11, 2003

(54) TOPICAL COMPOSITIONS WITH A REVERSIBLE PHOTOCHROMIC INGREDIENT

(75) Inventors: Anthony D. Gonzalez, Waldwick, NJ (US); Andrew H. Pechko, Ridgewood, NJ (US); Robert E. Kalafsky, Ogdensburg, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 10/014,167

(22) Filed: Dec. 11, 2001

(51) Int. Cl.⁷ .............. A61K 7/42; A61K 7/32; A61K 31/74; A61K 7/00; A01N 28/00
(52) U.S. Cl. .............. 424/59; 424/63; 424/65; 424/78.02; 424/78.08; 424/400; 424/401; 424/405; 514/844; 514/937; 514/938
(58) Field of Search .............. 424/59, 400, 401, 424/78.02, 78.08, 63, 65, 405; 514/844, 937, 938

(56) References Cited

U.S. PATENT DOCUMENTS

| | | | |
|---|---|---|---|
| 4,666,949 A | 5/1987 | Shimizu et al. |
| 5,000,937 A | 3/1991 | Grollier et al. |
| 5,221,288 A | 6/1993 | Kamata et al. |
| 5,252,103 A | 10/1993 | Kamata et al. |
| 5,523,075 A | 6/1996 | Fuerst et al. |
| 5,532,029 A | 7/1996 | Fuerst et al. |
| 5,837,645 A | 11/1998 | Fuerst et al. |
| 5,916,541 A | 6/1999 | Stewart |
| 5,997,891 A | 12/1999 | Fuerst et al. |
| 6,139,821 A | 10/2000 | Fuerst et al. |

OTHER PUBLICATIONS

US 6,290,977, 9/2001, Friars et al. (withdrawn)

*Primary Examiner*—Shelley A. Dodson
(74) *Attorney, Agent, or Firm*—Ohlandt, Greeley, Ruggiero & Perle, LLP

(57) ABSTRACT

There are provided topical compositions having reversible visible change in color in response to change in light. The compositions comprise color changing capability provided by photochromic material and a vehicle acceptable for topical application to the skin or hair.

34 Claims, No Drawings

TOPICAL COMPOSITIONS WITH A REVERSIBLE PHOTOCHROMIC INGREDIENT

BACKGROUND OF THE INVENTION

1. Field of the Invention

The present invention relates to topical compositions having a reversible photochromic material that responds to light stimulus. More particularly, the present invention relates to compositions having a photochromic pigment that can be applied to the skin and/or hair in a variety of cosmetic, personal care, over-the-counter and pharmaceutical products. The present invention provides a consumer perceptible stimuli to indicate application/duration of product on the consumer, as well as for decorative purposes.

2. Description of the Prior Art

A variety of cosmetic, personal care, consumer and medicinal products, including over-the-counter and pharmaceutical products, could benefit by using visual calorimetric signals responsive to changes in light. For example, there is growing recognition of the fact that over-exposure to the sun's rays is instrumental in causing aging of the skin and the development of related medical conditions such as skin cancer. A variety of suncare products have been developed to help reduce the risks associated with exposure to the sun. For example, some products use color as an indicator to determine whether the product has been initially applied over the desired skin areas. Some such products go on colored and become invisible as they are rubbed into the skin.

A problem with such suncare products is determining whether product that was earlier applied is still present and providing protection from the sun. Typically, such products are formulated to be water-resistant. However, after exposure to water, and/or excessive perspiration, it is uncertain as to how much suncare product has worn off and how much remains effective on the skin. The present invention provides a solution to this problem and an easy way to determine where sunscreen or other personal care or other outdoor protection product has been removed (i.e., whether previously applied product is still present).

In addition to suncare products, colorimetric signals, particularly photochromic indicators, are useful for a number of commercial products, including but not limited to, oral care products, surfactant/cleaning products, over-the-counter drugs and pharmaceuticals, artificial tanning products, sporting camouflage, foot-care products, liquid and bar soaps, anti-perspirant and deodorant products, fragrance-emitting products, analgesics, insect repellents, poison ivy products including poison ivy blocks, jellyfish protectants, hair care products, shampoos, conditioners, hair colors, hair styling products, hair mascaras, and decorative cosmetics including various make-up products, pressed powder, mascara, eye liners, temporary and permanent tattoos, body art, lipsticks, lip gloss and lip balms.

Compositions containing temporary visual indicators activated by change in pH and methods of use are known in the art. For example, U.S. Pat. No. 5,523,075 to Fuerst, et al. is directed to suncare cosmetic compositions that contain the indicator phenolphthalein which can be seen when a composition is applied to the skin and thereafter becomes colorless in response to a pH change. The pH change is mediated by an ingredient, which alters pH following application to the skin.

U.S. Pat. No. 5,532,029 also to Fuerst, et al. is directed to a paint ball that responds to a change in pH by changing from one color to another, or changing from colorless to a color, or changing from a color to colorless. The paint balls contain a pH-modifying substance that effects the change in color upon contact with an object or person.

U.S. Pat. No. 5,837,645 to Fuerst, et al. is directed to a method for marking a surface with a temporary visual indicator, which involves a pH change mechanism. The method of this patent employs compositions that contain an indicator and a pH modifying substance. The indicator is invisible at an initial pH and becomes a visible color after application at a second pH. The pH modifying substance of the applied composition evaporates or degrades upon application. This effects a change in pH that causes the indicator to change from invisible to a visible color. The color change is not reversible.

U.S. Pat. No. 5,997,891 to Fuerst, et al. is directed to compositions, which change color in response to a pH change. Compositions for use as sunscreens, paints, lacquers, sealants, protectants, polishes, varnishes, herbicides, pesticides, fertilizers, antibacterials, antiseptics, topical dermatologicals, and ophthalmological sprays or lotions. Compositions of this patent have a temporary visual indicator that changes color in response to changes in pH. Changes from one color to another, from colorless to a visible color, and from visible color to colorless, are described.

U.S. Pat. No. 6,139,821 to Fuerst, et al. is directed to sunscreen compositions that contain a temporary visual indicator that changes color when applied to the skin. The visual indicators of the compositions of this patent change color in response to a pH change mediated by a volatile base ingredient. The base evaporates producing a pH change that produces a color change in the indicator.

Both thermochromic and photochromic materials are known in the art. With regard to thermochromic materials, which show reversible color changes in response to changes in temperature, compositions of three components, namely an acidic substance, an acid developing substance, and a solvent, are known. Concerning photochromic materials, conventional inorganic photochromic compounds, such as silver halides, are well known in the art. More recently, a wide variety of organic photochromic compounds, which show reversible color changes in response to changes in light, have been developed. Such organic photochromic compounds generally show more sensitive color changes between colored and colorless states and offer a diverse color selection. Also, these organic compounds are generally more suitable for addition to organic compositions than are conventional inorganic photochromic compounds.

U.S. Pat. No. 4,666,949 to Shimizu et al. is directed to thermochromic polyurethane foam compositions. The thermochromic compositions, which serve as the coloring agent of the polyurethanane foam, have three ingredients, an electron-donating chromogenic material, an acidic substance, and a solvent, which are enclosed in microcapsules.

U.S. Pat. No. 5,221,288 to Kamata et al. is directed to methodology for dyeing cellulose fiber textile products involving use of thermochromic material encapsulated in polymer microcapsules and/or photochromic material encapsulated in polymer microcapsules or in particles of a polymer matrix.

U.S. Pat. No. 5,252,103 to Kamata et al. is directed to methodology for pigmenting or dyeing cellulose fiber textile products. The methodology may utilize photochromic microcapsules or thermochromic microcapsules that provide reversible color changes.

U.S. Pat. No. 6,290,977 to Friars et al. provides flowable personal care compositions having a thermochromic pigment, and a methodology for sensing or recording the temperature of skin using compositions having a thermochromic pigment.

However, in spite of the variety of chemical materials that show color change in response to chemical or physical stimuli, there remains a need, especially in the cosmetic and personal care industries, for products that exhibit colorimetric signals in response to changes in light. More particularly, in view of the limitations and demands in these industries, there remains a need for products that show reversible visible color changes in response to changes in light.

SUMMARY OF THE INVENTION

It is an object of the present invention to provide compositions that incorporate visual indicators that respond to changes in environmental stimuli.

It is another object of the present invention to provide compositions having a visible color change in response to change in light intensity and/or wavelength.

It is still another object of the present invention to provide compositions having photochromic pigments that exhibit a reversible visible color change in response to a change in light intensity and/or wavelength and that are useful in cosmetics and personal care products.

It is a further object of the present invention to provide compositions having photochromic pigments that exhibit a reversible visible color change in response to a change in light intensity and wavelength to be useful in medical and pharmaceutical procedures.

These and other objects and advantages of the present invention and equivalents thereof, are achieved by topical compositions having a photochromic pigment that provides a visual color signal and exhibits reversible color change in response to a change in light intensity and wavelength, especially as a result of specific light-induced chemical changes in the chromophores.

DETAILED DESCRIPTION OF THE INVENTION

Generally, the present invention provides compositions incorporating a photochromic pigment and methods of use thereof. Compositions of the present invention provide a visual color signal, which changes color in response to a change in light stimuli. Such a color change is reversible. Basically, the present compositions are signaling compositions that have the ability to resonate upon exposure or removal of required stimuli. These compositions are useful for a variety of personal care, hair care, cosmetic, and medicinal, such as over-the-counter and pharmaceutical, products.

Compositions of the present invention are preferably applied topically to the skin. They can also be applied to lips and/or hair. They provide a visual signal or indication of the location to which the composition is applied.

The present compositions are neither limited in form or with respect to the use of the photochromic pigment. Those skilled in the art of product formulation can with facility incorporate a photochromic pigment into all types of products, such as, for example, surfactant/cleaning systems, oral care products, over-the-counter drugs, artificial tanning products, suncare/beach products, foot-care products, liquid and bar soaps, sporting camouflage, anti-perspirant and deodorant products, fragrance-emitting products, analgesics, poison ivy products including poison ivy blocks, jellyfish protectants, insect repellents, cosmetic stick products, hair care products such as conditioners, shampoos, hair colors and hair styling aids, hair mascaras, decorative cosmetics such as make-ups, pressed powders, mascaras, eyeliners, tattoos, body art, lipsticks, lip glosses, and lip balms, and athletic products such as undereye block (i.e. anti-glare) worn by skiers, baseball, football and soccer players. Thus, the novel uses of phbtochromic pigments can produce formulations for a wide array of consumer, pharmaceutical and personal care products having visual color indication of various uses and functionalities.

For example, in suncare/beach products, a photochromic pigment can function as a visual signal or indicator of protection against ultraviolet radiation. This is also useful in artificial tanning beds where the consumer can be protected from overexposure to both UVA and UVB radiation. Suncare/beach products with photochromic pigments are preferably colorless in indoor light, especially low intensity indoor light, and become colored upon exposure to outdoor light. This expression of color in outdoor light provides visual indication of the skin area to which the suncare product has been applied and assurance that the consumer is protected from UV rays. As the sun protection efficacy of the product fades due to wash off from beach swimming or general wearing of the product, the color intensity of the product in outdoor light will commensurately fade. Thus, the user is able to know where re-applications are necessary. Another advantage of the present invention is that the color changes are reversible and will return to their normal (clear) color in the absence of UV light (i.e. indoor light). This provides a novel and particularly interesting visual effect, which is surprising and pleasing to the user and to those within his or her presence. For example, parents on summer vacation will typically apply a sunscreen product to their young children inside their hotel room or vacation home, before stepping outside to the beach or outdoor pool. In indoor light, the sunscreen product on the child will be clear, a clear color, or colorless. However, once exposed to outdoor light, the child's skin (face, arms, torso and legs) to which the product has been applied will turn a bright color, such as blue, red, green, teal, purple, pink, yellow, orange, or other color. The child can be a spectacle of fun and amusement outdoors, but as the child re-enters the hotel lobby or other indoor space, the color will disappear. Thus, the product simultaneously provides an exciting, new experience and visual effect, as well as a visual signal of the duration of the product's efficacy. In addition, the compositions of the present invention may change to different colors or shade of a color in response to different intensities of light, as the color fades, or as the sunscreen efficacy of the composition fades. As used herein, the term "indoor light" means artificial light other than direct natural sun light, and "low intensity indoor light" means less than about 1 Joule/$cm^2$.

In some compositions of the present invention, including but not limited to insect repellant products and other outdoor protection products, it is preferred that the photochromic material be colorless (i.e., in its resting or non-excited state) when exposed to indoor or low light intensity and colored (i.e., in its excited state) when exposed to outdoor light intensity. With such compositions, the photochromic material is colorless or one color at a light intensity less than about 5 Joules/$cm^2$, preferably less that about 2 Joules/$cm^2$, and most preferably less that about 1 Joule/$cm^2$. The photochromic material is colored or a second color at a light intensity greater that about 1 Joule/$cm^2$, preferably greater than about 2 Joules/cm², and most preferably greater than about 5 Joules/cm².

In another embodiment of the present invention, the present composition would function opposite the sunscreen embodiment in that the present composition would be clear or colorless in outdoor light, yet would be colored in indoor light. For example, when used in medical and/or pharmaceutical applications, the present compositions can be topically applied as an anti-bacterial or anesthetic during outpatient surgery to indicate duration/wear of the antibacterial/anesthetic. The applied composition will remain colored during the length of the surgery to indicate that, for example, the anesthetic is still taking effect. As the color intensity begins to fade, the surgeon will know that the effect of the anesthetic is beginning to wear off. However, even if the surgery is completed before the composition wears off, it will become clear or colorless when the person exits the outpatient facility to outdoor light. With such compositions, the photochromic material is colorless at a light intensity greater that about 1 Joule/cm², preferably greater than about 2 Joules/cm², and most preferably greater than about 5 Joules/cm². Also, the photochromic material is colored at a light intensity less than about 5 Joules/cm², preferably less that about 2 Joules/cm² and most preferably less that about 1 Joule/cm².

The photochromic material of the present invention is preferably an organic photochromic compound. The organic photochromic compound may be in the form of a matrix or microcapsule. A matrix can be produced by dispersing photochromic compound in an appropriate medium. Microcapsules can be obtained by microencapsulating the organic photochromic material in solution or as a fine grain dispersion in a medium. Microcapsules of photochromic material are preferably about 1 μm to to about 10 μm in diameter.

Selected photochromic capsules are available from Matsui Shikiso Chemical Co., Ltd. For example, PHOTOPIA BLUE is a microcapsule of 6 μm average particle diameter that has organic photochromic compound.

Organic photochromic compounds that can be used in the present compositions include, but are not limited to, azobenzene compounds, thioindigo compounds, dithizone metal complexes, spiropyran compounds, spirooxazine compounds, napthopyran compounds, fulgide compounds, dihydropyrene compounds, spirothiopyran compounds, 1,4-2H-oxazine, triphenylmethane compounds, viologen compounds, or any combinations thereof.

Organic photochromic compounds that are preferably used in the invention include, but are not limited to, 1,3,3-trimethylspiro[indolino-2,3'(3H)naphtho(2,1-b)(1,4,)-oxazine]; 5-methoxy-1,3,3-trimethylspiro[indolino-2,3'-(3H)naptho(2,1-b)(1,4)-oxazine]; 5-chloro-1,3,3-trimethylspiro[indolino-2,3'-(3H)naphtho(2,1-b)(1,4)-oxazine]; 8'-piperidino-1,3,3-trimethylspiro[indolino-2,3'-(3H)naphtho(2,1-b)(1,4)-oxazine]; 1-benzyl-3,3-dimethyspiro[indolino-2,3'-d(3H)naphtho(2,1-b)(1,4)-oxazine]; 1,3,5,6,-tetramethyl-3-ethylspiro[indolino-2,3'-(3H)naphtho(2,1-b)(1,4)-oxazine]; 1,3,3,5,6-pentamethylspiro[indolino-2,3'-(3H)naphtho(2,1-b)(1,4)oxazine]; 1,3',3'-trimethylspiro(2H-1benzopyran-2,2'-indolino); 3,3,1-diphenyl-3H-naphtho-(2,1,1-b)pyran; 1,3,3-triphenylspiro[indolino-2,3'-(3H)naphtho(2,1-b)pyran]; 1-(2,3,4,5,6-pentamethylbenzyl)-3,3-dimethylspiro[indolino-2,3'-(3H)-naphtho(2,1-b)pyran]; 1-(2-nitrobenzyl)-3,3-dimethylspiro[indolino-2,3'-(3H)-naphtho(2,1-b)pyran]; 1,1-diphenylnaphthopyran, 2,5-dimethylfuryl-trimethyfulgide, 2-methyl-5-chlorotrimethylfulgide, or any combinations thereof.

Photochromic and thermochromic material may be used in combination. By the combined use of thermochromic and photochromic material in the present invention, the visible color of the product shows reversible color changes in response to variations in temperature and in the presence or absence of light.

The amount of the color signal ingredient in the compositions of the present invention is preferably an amount sufficient to effect a visible color change in response to a change in light. On a weight percentage basis, the amount of the active pigment ingredient having photochromic material alone or a combination of thermochromic and photochromic materials, in the final present compositions ranges from about 0.01 percentage by weight (wt %) to about 40 wt %, preferably about 0.05 wt % to about 25 wt %, and most preferably about 0.75 wt % to about 10 wt %, based on the total weight of the composition. The amount within the range will vary based upon the type of vehicle. For example, a vehicle that impinges upon the photochromic material will require the composition to have a greater amount of photochromic material, e.g. the amount will be towards the high end of the range.

Photochromic pigment compositions are believed especially useful for a variety of cosmetic products. Cosmetic compositions having a photochromic pigment can be used with body or skin art. A visible color change, which is reversible, would result with a change in exposure to light to produce a novel skin appearance. They may also be used to enhance the color of a lipstick, eye and other make-ups. Visible color change would reversibly occur when going back and forth between different light patterns such as a passage from indoors to outdoors or upon exposure to artificially produced ultra violet or other light source. The use of photochromic pigments with a lipstick, a lip balm or other compositions applied to the lips, are especially preferred applications.

Photochromic pigments can also be used in hair care products to enhance natural or dyed hair pigments with reversible color changes when going back and forth from indoors to outdoors or upon exposure to "black" light or other specific wavelength of light.

In perfumes or other fragrance-emitting products, photochromic pigments can also be used. Such products could show reversible visible color changes with changes in "mood" responsive to changes in light.

The product form of the present compositions may be an aerosol, cream, emulsion, gel, liquid, lotion, mousse, patch, pomade, powder, solid, spray, stick or towelette. The compositions may also include a vehicle acceptable for topical application to the skin or hair. Examples of such vehicles include, but are not limited to, water and aqueous systems; glycerin; various hydrophilic solvents including alcohols such as ethanol, methanol, propyl and other alcohols; or any combinations thereof. In addition, the vehicle of the compositions according to the present invention can be in the form of a suspension, solution, mixture, homogeneous phase formulation or in the form of an emulsion, including, but not limited to, oil-in-water, water-in-oil and multiple phase emulsions. These emulsions can cover a broad range of consistencies including a thin lotion (which can also be suitable for spray or aerosol delivery), creamy lotion, light cream, and heavy cream. Other suitable topical carriers include an anhydrous liquid solvent such as oil and alcohol; aqueous-based single phase liquid solvent (e.g. hydroalcoholic solvent system); anhydrous solid and semisolid (such as a gel and a stick); and aqueous based gel and mousse system.

Where the photochromic materials are soluble or dispersible in an aqueous medium, the formulation may be aqueous based. Where the photochromic materials are hydrophobic, they may be mixed into a hydrophobic matrix, which is then blended into water to produce an oil-in-water type emulsion. The pH of these oil-in-water emulsion compositions is preferably in the range about 4.5 to about 9. Additionally, the mean particle size of the dispersed oil phase materials (e.g. sunscreen agent, polymer, perfumes, etc.) dispersed in the aqueous phase of these oil-in-water emulsion compositions may be in the range about 5 to about 10 microns with greater than about 75% of the particles being less than about 12 microns.

The present compositions may also contain one or more insect repellent actives. The insect repellent active employed in the present composition may be any oil-soluble active known in the art. The compositions may be administered in preparation for a variety of outdoor activities, such as picnicking, fishing, hiking and exercise. Depending upon the product form, the compositions may be administered to clothing, as well as to skin. Such actives include, but are not limited to, N,N diethyl-m-toluamide (DEET), ethyl butylacetylaminopropionate (IR3535 by Merck Co.), hydroxyethyl isobutyl piperidine carboxylate (1-piperidine carboxylic acid) (Bayer KBR 3023), oil of citronella, soy bean oil, lemon grass oil, geranium/geraniol oil, neem oil and other natural essential oils, p-menthane-3,8-diol, or any mixtures thereof. Other useful actives are disclosed in U.S. Pat. Nos. 5,130,136 and 5,698,209, which patents are incorporated herein by reference. Preferred insect repellent actives are DEET, IR3535, p-menthane-3,8-diol and oil of citronella.

The insect repellent active is present in an amount about 0.05 wt % to about 90 wt %, preferably about 0.1 wt % to about 50 wt %, and most preferably about 0.1 wt % to about 30 wt %, based on the total weight of the composition.

The present compositions, with or without an insect repellent, may have one or more sunscreen actives. Sunscreen actives that can be used include those for UVA and UVB protection (290 to 400 nanometer solar radiation). The sunscreen active may be any organic or inorganic compound known in the art such as oxybenzone, sulisobenzone, dioxybenzone, menthyl anthranilate, para aminobenzoic acid (PABA), octyl methoxycinnamate, octocrylene, DEA methoxycinnamate, drometrizole trisiloxane, octyl salicylate, homomenthyl salicylate, octyl dimethyl PABA, TEA salicylate, titanium dioxide, zinc oxide, butylmethoxy dibenzoylmethane (avobenzone), 4-methyl benzilidene camphor, octyl triazone, terephthalydiene dicamphor sulfonic acid, ethyl PABA, hydroxy methylphenyl benzotriazole, methylene bis-benzotriazoyltetramethylbutylphenol, bis-ethylhexyloxyphenol methoxyphenol triazine, and mixtures of the foregoing. Other sunscreen actives that can be used include those disclosed in U.S. Pat. No. 5,000,937, which is incorporated herein.

Typically, sunscreen actives can range from about 0.1 wt % to about 80 wt %, and more preferably about 1 wt % to about 30 wt %, based on the total weight of the composition. The present composition can be formulated to deliver from about 2 to about 70 SPF in sunscreen protection, more preferably about 15 to about 30 SPF.

The present compositions may have a film former to improve water, sweat and wear resistance. The film former leaves a protective film on the surface of the skin either immediately or upon evaporation of volatiles in the composition. The film former can also enhance the spread characteristics of the composition, which allows the composition to be more uniformly and consistently applied to the skin. Further when used with an insect repellent and/or sunscreen active, the film former can help maintain the insect repellent and/or sunscreen active at the surface of the skin for a longer period of time than it would otherwise remain without the film former. Still further, the film former affords controlled release of the insect repellent and/or sunscreen active. The amount of film former ranges from about 0.01 wt % to about 30 wt %, and more preferably about 0.5 wt % to about 20 wt %, based on the total weight of the composition.

Film-formers that can be used in the present invention include, but are not limited to, one or more acrylate copolymers such as acrylate/octylacrylamide copolymers and acrylate/vinyl acetate copolymers; cellulosic polymers such as methyl cellulose and hydroxyethyl cellulose; ethylene/acrylic acid copolymer; polyacrylic acid; $C_1$ to $C_5$ alkyl galactomannan; isododecane/ethylene mixed copolymer; adipic acid/diethylene glycol/glycerin crosspolymer; trimethylpentanediol/adipic acid copolymer; trimethylpentanediol/adipic acid/isononanoic acid; PVP/hexadecene copolymer (e.g., Ganex V-216); PVP/eicosene copolymer (e.g., Ganex V-220); alpha olefin/isopropyl maleate/MA polymer; cycloalkyl methacrylate copolymer/isododecane trimethyl polysiloxane; octadecene/MA copolymer; PPG-12/SMDI copolymer; acrylates $C_{10}$ to $C_{30}$ alkyl acrylate crosspolymer; cetyl hydroxyethylcellulose; dimethiconol; dimethicone; diglycol/cyclohexane-dimethanol/isophthalates/sulfoisophthalate copolymer; polyethylene; waxes such as beeswax and botanical waxes; polyurethane resins; natural gums; or any combinations of these ingredients. The polyurethane resins include Polyurethane-1, Polyurethane-2, Polyurethane-4, Polyurethane-5, and mixtures thereof. These polyurethane resins are described in the International Cosmetic Ingredient Dictionary and Handbook, $8^{th}$ edition, Printed Edition Pages 1152–1153, which is incorporated herein by reference. Additional film formers include those set forth in U.S. Pat. No. 5,916,541, which is incorporated herein by reference.

Also, the present composition may optionally include one or more of the following additional ingredients: anesthetics, anti-allergenics, antifungals, antimicrobials, anti-inflammatories, antiseptics, chelating agents, colorants, depigmenting agents, emollients, exfollients, fragrances, humectants, lubricants, moisturizers, pharmaceutical agents, preservatives, skin protectants, skin penetration enhancers, stabilizers, surfactants, thickeners, viscosity modifiers, and vitamins.

The present invention will allow for a new era of consumer perceptible cosmetic and personal care products. In suncare and other OTC applications, light indicators incorporated directly into products can provide a level of consumer awareness and protection that has not been seen to date. In other personal care arenas, the present invention will change the way consumers use and perceive their personal care products.

Although the present invention describes in detail certain embodiments, it is understood that variations and modifications exist known to those skilled in the art that are within the present invention. Accordingly, the present invention is intended to encompass all such alternatives, modifications and variations that are within the scope of the invention as set forth in the following claims.

What is claimed is:

1. A topical composition having a reversible visible change in color in response to a change in light comprising:

at least one photochromic material; and a vehicle acceptable for topical application to skin or hair.

2. The composition of claim 1, wherein the composition is a product selected from the group consisting of oral care product, over-the-counter drug, over-the-counter pharmaceutical, suncare product, sunscreen product, artificial tanning product, sporting camouflage, foot-care product, liquid and bar soap, surfactant/cleaning product, antiperspirant product, deodorant product, fragrance product, insect repellant, poison ivy product, jellyfish protectant, cosmetic stick product, hair care product, hair conditioner, shampoo, hair color product, hair styling product, hair mascara, make-up product, cosmetic pressed powder product, mascara, eyeliner, rouge, tattoo product, body art product, lipstick, lip gloss and lip balm.

3. The composition of claim 1, wherein said at least one photochromic material is in an amount sufficient to effect the visible change in color in response to the change in light intensity and/or wavelength.

4. The composition of claim 1, wherein said at least one photochromic material is in an amount about 0.05 wt % to about 25 wt %, based on the total weight of the composition.

5. The composition of claim 1, wherein said photochromic material is in an amount about 0.01 wt % to about 40 wt %, based on the total weight of the composition.

6. The composition of claim 1, further comprising a thermochromic material.

7. The composition of claim 1, wherein said at least one photochromic material is in the form of a matrix or a microcapsule.

8. The composition of claim 1, wherein said at least one photochromic material is at least one compound selected from the group consisting of azobenzene compounds, thioindigo compounds, dithizone metal complexes, spiropyran compounds, spirooxazine compounds, napthopyran compounds, fulgide compounds, dihydropyrene compounds, spirothiopyran compounds, 1,4-2H-oxazine, triphenylmethane compounds, viologen compounds, and any combinations thereof.

9. The composition of claim 1, wherein said vehicle is selected from the group consisting of water, aqueous solvent system, aqueous-based single phase liquid solvent system, hydro-alcoholic solvent system, glycerin, anhydrous liquid solvent, oil, alcohol, and any combinations thereof.

10. The composition of claim 1, wherein the composition is in a form selected from the group consisting of an aerosol, cream, emulsion, gel, liquid, lotion, mousse, patch, pomade, powder, solid, spray, stick, towelette, and any combinations thereof.

11. The composition of claim 1, wherein the composition is colored on skin or hair when in outdoor light, and becomes substantially colorless when indoors.

12. The composition of claim 1, wherein the composition is clear on skin or hair when in outdoor light, and becomes substantially colored when indoors.

13. The composition of claim 1, further comprising an insect repellent active.

14. The composition of claim 13, wherein the insect repellent active is present in an amount about 0.05 wt % to about 90 wt % based on the total weight of the composition.

15. The composition of claim 13, wherein the insect repellent active is selected from the group consisting of N,N diethyl-m-toluamide, ethyl butylacetylaminopropionate, hydroxyethyl isobutyl piperidine carboxylate, neem oil, oil of citronella, soy bean oil, lemon grass oil, geranium/geraniol oil, p-menthane-3,8-diol, and any combinations thereof.

16. The composition of claim 1, further comprising a film-forming polymer.

17. The composition of claim 16, wherein said film-forming polymer is selected from the group consisting of acrylate copolymers, cellulosic polymers, ethylene/acrylic acid copolymer, polyacrylic acid, $C_1$ to $C_5$ alkyl galactomannan, isododecane/ethylene mixed copolymer, adipic acid/diethylene glycol/glycerin crosspolymer, trimethylpentanediol/adipic acid copolymer, trimethylpentanediol/adipic acid/isononanoic acid, PVP/hexadecene copolymer, PVP/eicosene copolymer, alpha olefin/isopropyl maleate/MA polymer, cycloalkyl methacrylate copolymer/isododecane trimethyl polysiloxane, octadecene/MA copolymer, PPG-12/SMDI copolymer, acrylates $C_{10}$ to $C_{30}$ alkyl acrylate crosspolymer, cetyl hydroxyethylcellulose, dimethiconol, dimethicone, diglycol/cyclohexane-dimethanol/isophthalates/sulfoisophthalate copolymer, polyethylene, waxes, polyurethane resins, natural gums, and any combinations thereof.

18. The composition of claim 16, wherein the film-forming polymer is present in an amount about 0.01 wt % to about 30 wt % based on the total weight of the composition.

19. The composition of claim 1, further comprising a suncreen.

20. The composition of claim 19, wherein the sunscreen is present in an amount about 1 wt % to about 30 wt % based on the total weight of the composition.

21. The composition of claim 19, wherein the sunscreen is selected from the group consisting of oxybenzone, sulisobenzone, dioxybenzone, menthyl anthranilate, para aminobenzoic acid, octyl methoxycinnamate, DEA methoxycinnamate, octocrylene, drometrizole trisiloxane, octyl salicylate, homomenthyl salicylate, octyl dimethyl PABA, TEA salicylate, titanium dioxide, zinc oxide, butylmethoxy dibenzoylmethane, 4-methyl benzilidene camphor, octyl triazone, terephthalydiene dicamphor sulfonic acid, ethyl PABA, hydroxy methylphenyl benzotriazole, methylene bis-benzotriazoyltetramethylbutylphenol, bis-ethylhexyloxyphenol methoxyphenol triazine, and any combinations thereof.

22. The composition of claim 1, wherein the composition is a personal care product, and wherein said at least one photochromic material is a first color when indoors and a second color when exposed to outdoor light.

23. The composition of claim 22, wherein said personal care product is a product selected from the group consisting of a suncare product, an insect repellant product, a poison ivy product, and any combinations thereof.

24. The composition of claim 11, wherein said at least one photochromic material is colorless at a light intensity less than about 1 Joule/cm$^2$, and colored at a light intensity greater than about 5 Joules/cm$^2$.

25. The composition of claim 12, wherein said at least one photochromic material is colored at a light intensity less than about 1 Joule/cm$^2$, and colorless at a light intensity greater than about 5 Joules/cm$^2$.

26. A method of changing the color of a composition applied topically to skin or hair, comprising:

applying topically the composition of claim 1 to the skin or hair; and providing a change in light intensity and/or wavelength to the composition.

27. The method of claim 26, wherein said composition is selected from the group consisting of oral care product, over-the-counter drug, over-the-counter pharmaceutical, suncare product, sunscreen product, artificial tanning product, sporting camouflage, foot-care product, liquid and bar soap, surfactant/cleaning product, anti-perspirant product, deodorant product, fragrance product, insect repellant, poison ivy product, jellyfish protectant, cosmetic stick product, hair care product, hair conditioner, shampoo, hair color product, hair styling product, hair mascara, make-up product, cosmetic pressed powder product, mascara, eyeliner, rouge, tattoo product, body art product, lipstick, lip gloss and lip balm.

28. The method of claim 26, wherein said at least one photochromic material is present in an amount sufficient to effect the visible change in color in response to the change in light.

29. The method of claim 26, wherein said at least one photochromic material is present in an amount about 0.01 wt % to about 40 wt % based on the total weight of the composition.

30. The method of claim 26, wherein the composition further comprises a thermochromic material.

31. The method of claim 26, wherein the composition is an oil-in-water emulsion.

32. The method of claim 26, wherein the composition further comprises an ingredient selected from group consisting of a sunscreen active, an insect repellent active, a film-former, and any combinations thereof.

33. The method of claim 26, wherein said vehicle is selected from the group consisting of water, aqueous solvent system, aqueous-based single phase liquid solvent system, hydro-alcoholic solvent system, glycerin, anhydrous liquid solvent, oil, alcohol, and any combinations thereof.

34. A method of providing a visual signal of sun and/or insect repellent protection to skin comprising topically applying to the skin a product that is colored on skin for as long as protection is present when in outdoor light, and becomes substantially clear in color when indoors while on the skin.

* * * * *